US012714365B2

(12) United States Patent
Ren et al.

(10) Patent No.: US 12,714,365 B2
(45) Date of Patent: Aug. 25, 2026

(54) ELECTRONIC DEVICE

(71) Applicant: GOERTEK TECHNOLOGY CO., LTD., Qingdao (CN)

(72) Inventors: Jianlei Ren, Qingdao (CN); Junjie Pan, Qingdao (CN)

(73) Assignee: GOERTEK TECHNOLOGY CO., LTD., Qingdao (CN)

( * ) Notice: Subject to any disclaimer, the term of this patent is extended or adjusted under 35 U.S.C. 154(b) by 238 days.

(21) Appl. No.: 18/610,844

(22) Filed: Mar. 20, 2024

(65) Prior Publication Data

US 2024/0215913 A1 Jul. 4, 2024

Related U.S. Application Data

(63) Continuation of application No. PCT/CN2022/102820, filed on Jun. 30, 2022.

(30) Foreign Application Priority Data

Dec. 30, 2021 (CN) ........................ 202111660468.X
Feb. 11, 2022 (CN) ........................ 202210129826.2

(51) Int. Cl.
*A61B 5/00* (2006.01)
*A61B 5/332* (2021.01)
(Continued)

(52) U.S. Cl.
CPC .............. *A61B 5/681* (2013.01); *A61B 5/332* (2021.01); *A61B 5/4872* (2013.01); *G04G 21/025* (2013.01); *G04G 21/08* (2013.01)

(58) Field of Classification Search
CPC ................................ A61B 5/681; A61B 5/332
See application file for complete search history.

(56) References Cited

U.S. PATENT DOCUMENTS 11,106,309 B1 * 8/2021 Trapero Martin ........................... G06F 3/041661
2016/0252980 A1 * 9/2016 Park ......................... G01D 5/56 345/184

(Continued)

FOREIGN PATENT DOCUMENTS

CN 107340709 A 11/2017
CN 207768368 U 8/2018

(Continued)

OTHER PUBLICATIONS

First Office Action in Corresponding Chinese Application No. 202210129826.2, dated Dec. 28, 2024; 14 pgs.

(Continued)

*Primary Examiner* — Carl H Layno
*Assistant Examiner* — Bryan Mcallister Lee
(74) *Attorney, Agent, or Firm* — HAUPTMAN HAM, LLP

(57) ABSTRACT

Disclosed are an electronic device. The electronic device includes a shell and a rotating frame rotatably provided outside a part of the shell. The rotating frame is provided with a first physiological monitoring electrode, a second physiological monitoring electrode, a first rotating frame conductive member, and a second rotating frame conductive member. A physiological monitoring circuit is provided in the shell, and the shell is provided with a first shell conductive member and a second shell conductive member, both of which are electrically connected to the physiological monitoring circuit respectively. In response to that the rotating frame rotates to a preset position relative to the shell, the first rotating frame conductive member is in contact with the first shell conductive member, and the second rotating frame conductive member is in contact with the second shell conductive member.

16 Claims, 9 Drawing Sheets

(51) Int. Cl.
*G04G 21/02* (2010.01)
*G04G 21/08* (2010.01)

(56) References Cited

U.S. PATENT DOCUMENTS

2019/0274565 A1* 9/2019 Soli .................... A61B 5/02438
2021/0037932 A1* 2/2021 Min .................... A61B 5/0006

FOREIGN PATENT DOCUMENTS

CN 110664398 A 1/2020
CN 110989322 A 4/2020
CN 112305902 A 2/2021
CN 112817224 A 5/2021
CN 213545052 U 6/2021
CN 113725030 A 11/2021
CN 114451880 A 5/2022
CN 217009816 U 7/2022

OTHER PUBLICATIONS

International Search Report and Written Opinion in Corresponding International Application No. PCT/CN2022/102820, mailed Oct. 10, 2022; 14 pgs.

* cited by examiner 201
101
102
303
302
505
501

ELECTRONIC DEVICE

CROSS-REFERENCE TO RELATED APPLICATIONS

The present application is a continuation application of International Application No. PCT/CN2022/102820, filed on Jun. 30, 2022, which claims priority to Chinese Patent Applications No. 202111660468.X, filed on Dec. 30, 2021, and No. 202210129826.2, filed on Feb. 11, 2022. The disclosures of the above-mentioned applications are incorporated herein by reference in their entireties.

TECHNICAL FIELD

The present application relates to the technical field of electronic products, and in particular to an electronic device.

BACKGROUND

At present, users interact with the smart watch generally by touching the screen or touching the screen and rotating buttons. This interaction method is relatively simple. If you need to find a common function, the search operation is more cumbersome; in addition, in scenarios where the user's hands are relatively wet, when touching the screen, there will not only be water stains on the screen but also a high rate of false touches. Watches with rotating buttons are often complained by users because the rotating buttons are small and inconvenient to operate, which seriously affects the user experience.

In the related art, the finger physiological electrodes of smart watches are generally provided on function buttons, and share a button with the function buttons. There are also electrodes of some watches that are equipped with a separate button. However, because physiological electrodes have requirements on the contact area, the electrode buttons are usually made larger, which affects the appearance of the smart watch. In addition, the positions of the electrode buttons are fixed, which affects the user's operating experience to a certain extent.

To sum up, how to provide an electronic device that can improve the user's operating experience is an urgent problem that those skilled in the art need to solve.

SUMMARY

The main purpose of the present application is to provide an electronic device. The first physiological monitoring electrode and the second physiological monitoring electrode can be electrically connected to the physiological monitoring circuit by rotating the rotating frame. user can directly press their fingers on the two different electrodes to perform physiological monitoring, making the monitoring process more convenient, thereby overcoming the disadvantages of high false touch rate and small buttons, and improving the user experience during operation.

In order to achieve the above purpose, the present application provides an electronic device, including:

a shell and a rotating frame rotatably provided outside a part of the shell;

the rotating frame is provided with a first physiological monitoring electrode, a second physiological monitoring electrode, a first rotating frame conductive member electrically connected to the first physiological monitoring electrode, and a second rotating frame conductive member electrically connected to the second physiological monitoring electrode;

a physiological monitoring circuit is provided in the shell, and the shell is provided with a first shell conductive member electrically connected to the physiological monitoring circuit and a second shell conductive member electrically connected to the physiological monitoring circuit; and in response to that the rotating frame rotates to a preset position relative to the shell, the first rotating frame conductive member is in contact with the first shell conductive member, and the second rotating frame conductive member is in contact with the second shell conductive member, so that the first physiological monitoring electrode and the second physiological monitoring electrode are electrically connected to the physiological monitoring circuit respectively.

In some embodiments, the physiological monitoring circuit is an electrocardiogram (ECG) monitoring circuit; and in response to that the rotating frame rotates to a first position relative to the shell, the first rotating frame conductive member is in contact with the first shell conductive member, and the second rotating frame conductive member is in contact with the second shell conductive member, so that the first physiological monitoring electrode and the second physiological monitoring electrode are electrically connected to the ECG monitoring circuit respectively.

In some embodiments, the physiological monitoring circuit is an ECG monitoring circuit; and in response to that the rotating frame rotates to a first position relative to the shell, the first rotating frame conductive member is in contact with the first shell conductive member, and the second rotating frame conductive member is in contact with the second shell conductive member, so that the first physiological monitoring electrode or the second physiological monitoring electrode are electrically connected to the ECG monitoring circuit.

In some embodiments, the physiological monitoring circuit is a body fat monitoring circuit; and in response to that the rotating frame rotates to a second position relative to the shell, the first rotating frame conductive member is in contact with the first shell conductive member, and the second rotating frame conductive member is in contact with the second shell conductive member, so that the first physiological monitoring electrode and the second physiological monitoring electrode are electrically connected to the body fat monitoring circuit respectively.

In some embodiments, the physiological monitoring circuit includes an ECG monitoring circuit and a body fat monitoring circuit; the first shell conductive member includes a first ECG conductive member electrically connected to the ECG monitoring circuit and a first body fat conductive member electrically connected to the body fat monitoring circuit, and the second shell conductive member includes a second ECG conductive member electrically connected to the ECG monitoring circuit and a second body fat conductive member electrically connected to the body fat monitoring circuit;

in response to that the rotating frame rotates to a first position relative to the shell, the first rotating frame conductive member is in contact with the first ECG conductive member, and the second rotating frame conductive member is in contact with the second ECG conductive member, so that the first physiological monitoring electrode and the second physiological monitoring electrode are electrically connected to the ECG monitoring circuit respectively; and in response to that the rotating frame rotates to a second position relative to the shell, the first rotating frame conductive member is in contact with the first body fat conductive member, and the second rotating frame conductive member is in contact with the second body fat conductive member, so that the first physiological monitoring electrode and the second physiological monitoring electrode are electrically connected to the body fat monitoring circuit respectively.

In some embodiments, the physiological monitoring circuit includes an ECG monitoring circuit and a body fat monitoring circuit; the first shell conductive member includes a third ECG conductive member electrically connected to the ECG monitoring circuit and a first body fat conductive member electrically connected to the body fat monitoring circuit, and the second shell conductive member includes a second body fat conductive member electrically connected to the body fat monitoring circuit;

in response to that the rotating frame rotates to a first position relative to the shell, the first rotating frame conductive member is in contact with the third ECG conductive member, so that the first physiological monitoring electrode is electrically connected to the ECG monitoring circuit; and in response to that the rotating frame rotates to a second position relative to the shell, the first rotating frame conductive member is in contact with the first body fat conductive member, and the second rotating frame conductive member is in contact with the second body fat conductive member, so that the first physiological monitoring electrode and the second physiological monitoring electrode are electrically connected to the body fat monitoring circuit respectively.

In some embodiments, the second shell conductive member includes a connecting member; and in response to that the rotating frame rotates to the first position relative to the shell, the first rotating frame conductive member is in contact with the third ECG conductive member, and the connecting member is in contact with the second rotating frame conductive member.

In some embodiments, the physiological monitoring circuit includes an ECG monitoring circuit and a body fat monitoring circuit;

the first shell conductive member and the second shell conductive member are connected to the ECG monitoring circuit or the body fat monitoring circuit through a switch; when the rotating frame rotates relative to the shell to a position where the first rotating frame conductive member is in contact with the first shell conductive member, and the second rotating frame conductive member is in contact with the second shell conductive member:

in response to that the switch is switched to a position where the first shell conductive member and the second shell conductive member are connected to the ECG monitoring circuit, the first physiological monitoring electrode and the second physiological monitoring electrode are electrically connected to the ECG monitoring circuit respectively; and in response to that the switch is switched to a position where the first shell conductive member and the second shell conductive member are connected to the body fat monitoring circuit, the first physiological monitoring electrode and the second physiological monitoring electrode are electrically connected to the body fat monitoring circuit respectively.

In some embodiments, the physiological monitoring circuit includes an ECG monitoring circuit and a body fat monitoring circuit;

the first shell conductive member and the second shell conductive member are connected to the ECG monitoring circuit or the body fat monitoring circuit through a switch; when the rotating frame rotates relative to the shell to a position where the first rotating frame conductive member is in contact with the first shell conductive member, and the second rotating frame conductive member is in contact with the second shell conductive member:

in response to that the switch is switched to a position where the first shell conductive member is connected to the ECG monitoring circuit, the first physiological monitoring electrode is electrically connected to the ECG monitoring circuit; and in response to that the switch is switched to a position where both the first shell conductive member and the second shell conductive member are connected to the body fat monitoring circuit, the first physiological monitoring electrode and the second physiological monitoring electrode are electrically connected to the body fat monitoring circuit respectively.

In some embodiments, an insulator is provided between the first physiological monitoring electrode and the second physiological monitoring electrode to prevent the first physiological monitoring electrode from contacting and conducting the second physiological monitoring electrode.

In some embodiments, part of the rotating frame is made of metal, and the first physiological monitoring electrode and the second physiological monitoring electrode are respectively the part of the rotating frame made of metal.

In some embodiments, the shell is made of insulating material; or at least one of a surface of the rotating frame contacting the shell and a surface of the shell contacting the rotating frame is provided with an insulating coating.

In some embodiments, both the first rotating frame conductive member and the second rotating frame conductive member are protrusions provided on the rotating frame, and both the first shell conductive member and the second shell conductive member are spring pins.

In some embodiments, the protrusions are provided with an inclined surface in contact with the spring pins.

In some embodiments, the electronic device further includes:

a gear limiting mechanism including at least one elastic component and at least one groove for cooperating with the at least one elastic component;

one of the elastic component and the groove is provided on the shell, and the other of the elastic component and the groove is provided on the rotating frame, and in response to that the rotating frame rotates to a preset position relative to the shell, the elastic component is engaged with the corresponding groove.

In some embodiments, the shell is provided with a guide chute with an annular part; a side of the rotating frame facing the shell is provided with a guide protrusion cooperated with the guide chute, and the guide protrusion is configured to insert into the guide chute and slide along the guide chute.

In some embodiments, the electronic device is a smart watch; the smart watch further includes a dial provided on the shell, and the rotating frame is configured to surround the dial.

In the process of using the electronic device provided by the present application, when it is necessary to monitor physiological characteristics, the rotating frame first needs to be rotated until the first rotating frame conductive member is in contact with the first shell conductive member, and the second rotating frame conductive member is in contact with the second shell conductive member so that the first physiological monitoring electrode and the second physiological monitoring electrode electrically connected to the physiological monitoring circuit respectively. At this time, an user can press her/his finger onto the first physiological monitoring electrode and the second physiological monitoring electrode respectively, so that the human body and the physiological monitoring circuit are electrically connected to monitor the relevant physiological data.

Compared with the related art, the electronic device provided by the present application is simple and convenient to complete the process of physiological monitoring. The user just rotates the rotating frame so that the first physiological monitoring electrode and the second physiological monitoring electrode electrically connected to the physiological monitoring circuit respectively, which avoids directly touching the screen, and the first physiological monitoring electrode and the second physiological monitoring electrode are both provided on the rotating frame, making it convenient to directly press the finger on the first physiological monitoring electrode and the second physiological monitoring electrode, thereby improving the user's experience during operation.

BRIEF DESCRIPTION OF THE DRAWINGS

In order to more clearly illustrate the technical solutions in the embodiments of the present application or in the related art, a brief introduction will be given to the accompanying drawings required in the description of the embodiments or the related art. Obviously, the accompanying drawings in the following description are only some embodiments of the present application. For those skilled in the art, other accompanying drawings can be obtained based on the structures shown in these drawings without any creative effort.

Figure 1:
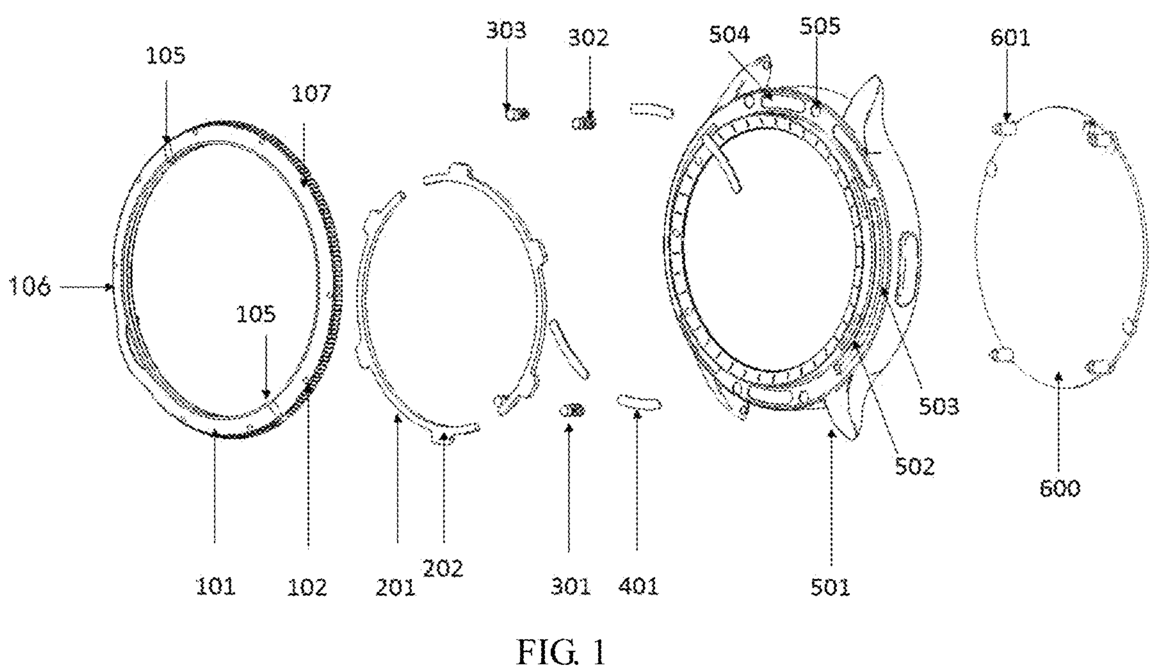
FIG. 1 is a schematic exploded view of an electronic device according to some embodiments of the present application.

The realization of the purpose, functional characteristics and advantages of the present application will be further described with reference to the attached drawings in combination with embodiments.

DETAILED DESCRIPTION OF THE EMBODIMENTS

The technical solutions of embodiments of the present application will be clearly and completely described with reference to the drawings in the embodiments of the present application. Obviously, the described embodiments are only some rather than all of the embodiments of the present application. Based on the embodiments of the present application, all other embodiments obtained by those skilled in the art without creative efforts shall fall within the scope of the present application.

The present application is to provide an electronic device that can make the first physiological monitoring electrode and the second physiological monitoring electrode electrically connected to the physiological monitoring circuit respectively by rotating the rotating frame, and the user can directly press the finger on the two different electrodes to perform physiological monitoring, which makes the monitoring process more convenient, overcomes the disadvantages of high false touch rate of the touch screen or small buttons, and improves the user experience during operation. In addition, there is no need to provide additional buttons as electrodes, making the layout of the electronic device more reasonable, which is conducive to improving the aesthetics of the product.

As shown in FIG. 1 to FIG. 17, the present application provides an electronic device. The electronic device can be wearable electronic devices such as smart watches, smart bracelets, smart rings, smart necklaces, head-mounted displays, smart glasses, etc. It can also be locators, mobile phones, smart speakers, game controller etc.

The electronic device includes a shell 501 and a rotating frame 101 rotatably provided outside a part of the shell 501.

The rotating frame 101 is provided with a first physiological monitoring electrode 106, a second physiological monitoring electrode 107, a first rotating frame conductive member 103 electrically connected to the first physiological monitoring electrode 106, and a second rotating frame conductive member 104 electrically connected to the second physiological monitoring electrode 107.

A physiological monitoring circuit is provided in the shell 501, and the shell 501 is provided with a first shell conductive member and a second shell conductive member, both of which are electrically connected to the physiological monitoring circuit respectively.

In response to that the rotating frame 101 rotates to a preset position relative to the shell 501, the first rotating frame conductive member 103 is in contact with the first shell conductive member, and the second rotating frame conductive member 104 is in contact with the second shell conductive member, so that the first physiological monitoring electrode 106 and the second physiological monitoring electrode 107 are electrically connected to the physiological monitoring circuit respectively.

The first physiological monitoring electrode 106 and the second physiological monitoring electrode 107 may be electrode structures provided on the rotating frame 101, or may be part of the rotating frame 101, which is determined based on the actual situation.

There can be one physiological monitoring circuit or a plurality of physiological monitoring circuits, which are determined according to the actual situation.

It should be noted that in the process of measuring physiological data with contact electrodes, a plurality of electrodes are generally provided, some of which are placed in contact with the wrist and other wearing parts of the human body, and some of which are placed in non-contact positions.

During using the electronic device provided by the present application, when it is necessary to monitor physiological characteristics, the rotating frame 101 first needs to be rotated until the first rotating frame conductive member 103 contacts the first shell conductive member, and the second rotating frame conductive member 104 is in contact with the second shell conductive member, so that the first physiological monitoring electrode 106 and the second physiological monitoring electrode 107 are electrically connected to the physiological monitoring circuit respectively. At this time, you can press your fingers on the first physiological monitoring electrode 106 the second physiological monitoring electrode 107 respectively. In this way, the human body and the physiological monitoring circuit are electrically connected to complete the monitoring of relevant physiological data.

Compared with the related art, the electronic device provided by the present is simple and convenient to complete physiological monitoring, and during the operation, only the rotating frame 101 is required to rotate so that the first physiological monitoring electrode 106 and the second physiological monitoring electrodes 107 are electrically connected to the physiological monitoring circuit respectively, which avoids directly touching the screen in the related art. In addition, the first physiological monitoring electrode 106 and the second physiological monitoring electrode 107 are both provided on the rotating frame 101 to facilitate direct pressing fingers on the first physiological monitoring electrode 106 and the second physiological monitoring electrode 107, such that the user's experience during operation is improved. In addition, compared with the method provided with buttons, the size of the rotating frame 101 can be provided larger, which is convenient for operation and can avoid accidental touches.

In some embodiments, the physiological monitoring circuit is an electrocardiogram (ECG) monitoring circuit 8, in response to that the rotating frame 101 rotates to a first position relative to the shell 501, the first rotating frame conductive member is in contact with the first shell conductive member, and the second rotating frame conductive member is in contact with the second shell conductive member, so that the first physiological monitoring electrode 106 and the second physiological monitoring electrode 107 are electrically connected to the ECG monitoring circuit 8 respectively.

During use, by rotating the rotating frame 101, the first physiological monitoring electrode 106 and the second physiological monitoring electrode 107 can be electrically connected to the ECG monitoring circuit 8 respectively, thereby facilitating the detection of electrocardiogram.

In some embodiments, the physiological monitoring circuit is an ECG monitoring circuit 8, in response to that the rotating frame 101 rotates to a first position relative to the shell 501, the first rotating frame conductive member 103 is in contact with the first shell conductive member, and the second rotating frame conductive member 104 is in contact with the second shell conductive member, so that the first physiological monitoring electrode 106 or the second physiological monitoring electrode 107 is electrically connected to the ECG monitoring circuit 8. During use, by rotating the rotating frame 101, the first physiological monitoring electrode 106 can be electrically connected to the ECG monitoring circuit 8; or the second physiological monitoring electrode 107 can be electrically connected to the ECG monitoring circuit 8, which facilitates the detection of electrocardiogram.

In some embodiments, the physiological monitoring circuit is a body fat monitoring circuit 9, in response to that the rotating frame 101 rotates to a first position relative to the shell 501, the first rotating frame conductive member 103 is in contact with the first shell conductive member, and the second rotating frame conductive member 104 is in contact with the second shell conductive member, so that the first physiological monitoring electrode 106 and the second physiological monitoring electrode 107 are electrically connected to the body fat monitoring circuit 9 respectively.

During use, by rotating the rotating frame 101, the first physiological monitoring electrode 106 and the second physiological monitoring electrode 107 can be electrically connected to the body fat monitoring circuit 9 respectively, thereby facilitating the measurement of body fat.

In some embodiments, the physiological monitoring circuit is the body fat monitoring circuit 9, and the rotating frame 101 rotates to the second position relative to the shell 501. The physiological monitoring circuit mentioned in these previous embodiments is the ECG monitoring circuit 8, and the rotating frame 101 rotates to the first position relative to the shell 501 to the first position, the first position and the second position mentioned in these embodiments may be the same position or different positions, which are determined according to the actual situation.

In some embodiments, the physiological monitoring circuit includes an ECG monitoring circuit 8 and a body fat monitoring circuit 9, the first shell conductive member includes a first ECG conductive member electrically connected to the ECG monitoring circuit 8 and a first body fat conductive member 603 electrically connected to the body fat monitoring circuit 9, and the second shell conductive member includes a second ECG conductive member electrically connected to the ECG monitoring circuit 8 and a second body fat conductive member 604 electrically connected to the body fat monitoring circuit 9;

in response to that the rotating frame 101 rotates to a first position relative to the shell 501, the first rotating frame conductive member is in contact with the first ECG conductive member, and the second rotating frame conductive member is in contact with the second ECG conductive member, so that the first physiological monitoring electrode 106 and the second physiological monitoring electrode 107 are electrically connected to the ECG monitoring circuit 8 respectively; and in response to that the rotating frame 101 rotates to a second position relative to the shell 501, the first rotating frame conductive member is in contact with the first body fat conductive member 603, and the second rotating frame conductive member is in contact with the second body fat conductive member 604, so that the first physiological monitoring electrode 106 and the second physiological monitoring electrode 107 are electrically connected to the body fat monitoring circuit 9 respectively.

It should be noted that the first position and the second position mentioned in these embodiments are different positions.

During use, by rotating the rotating frame 101, the first physiological monitoring electrode 106 and the second physiological monitoring electrode 107 can be electrically connected to the ECG monitoring circuit 8 or the body fat monitoring circuit 9 respectively, so as to facilitate the measurement of electrocardiogram or body fat.

In some embodiments, the physiological monitoring circuit includes an ECG monitoring circuit 8 and a body fat monitoring circuit 9, the first shell conductive member includes a third ECG conductive member 601 electrically connected to the ECG monitoring circuit 8 and a first body fat conductive member 603 electrically connected to the body fat monitoring circuit 9, and the second shell conductive member includes a second body fat conductive member 604 electrically connected to the body fat monitoring circuit 9;

in response to that the rotating frame 101 rotates to a first position relative to the shell 501, the first rotating frame conductive member is in contact with the third ECG conductive member 601, so that the first physiological monitoring electrode 106 is electrically connected to the ECG monitoring circuit 8; and in response to that the rotating frame 101 rotates to a second position relative to the shell 501, the first rotating frame conductive member 103 is in contact with the first body fat conductive member 603, and the second rotating frame conductive member 104 is in contact with the second body fat conductive member 604, so that the first physiological monitoring electrode 106 and the second physiological monitoring electrode 107 are electrically connected to the body fat monitoring circuit 9 respectively.

It should be noted that the first position and the second position mentioned in these embodiments are different positions.

in some embodiments, a circuit board 600 can be provided in the shell 501, and the physiological monitoring circuit is provided in the circuit board 600.

During use, by rotating the rotating frame 101, the first physiological monitoring electrode 106 and the ECG monitoring circuit 8 can be electrically connected, or the first physiological monitoring electrode 106 and the second physiological monitoring electrode 107 can be electrically connected to the body fat monitoring circuit 9. It is convenient to measure electrocardiogram or body fat.

In some embodiments, considering balance and comfort during physiological monitoring, the second shell conductive member includes a third ECG conductive member 601 and a connecting member 602. In response to that the rotating frame 101 rotates to the first position relative to the shell 501, the first rotating frame conductive member 103 is in contact with the third ECG conductive member 601, and the connecting member 602 is in contact with the second rotating frame conductive member 104. The connecting member 602 may be a conductive member or an insulator, which is determined based on the actual situation.

Figure 3:
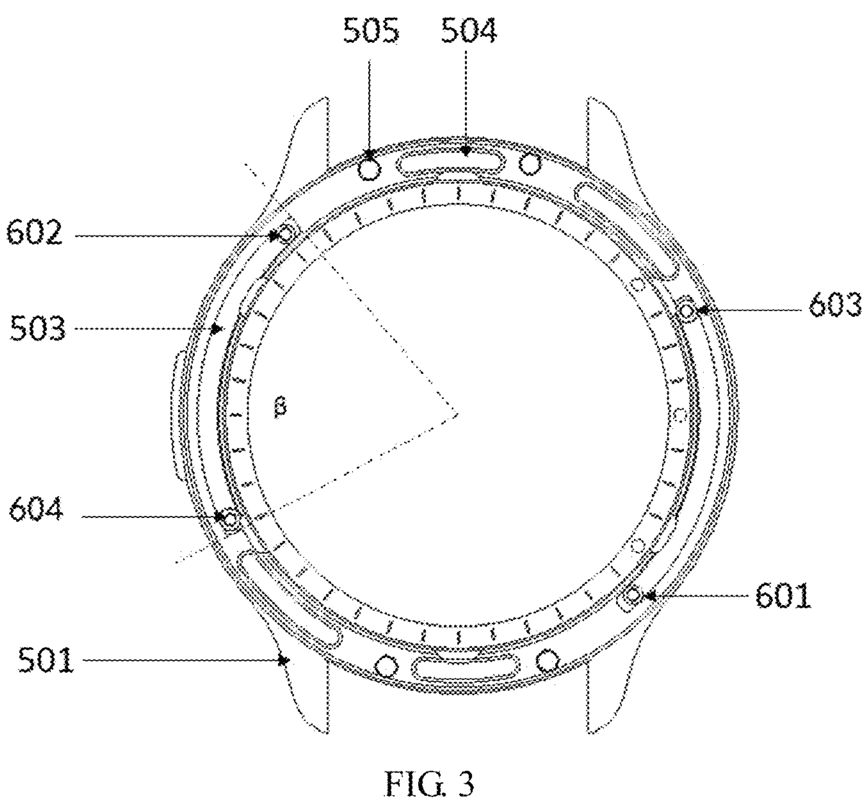
FIG. 3 is a schematic front view of a shell according to some embodiments of the present application.
Figure 4:
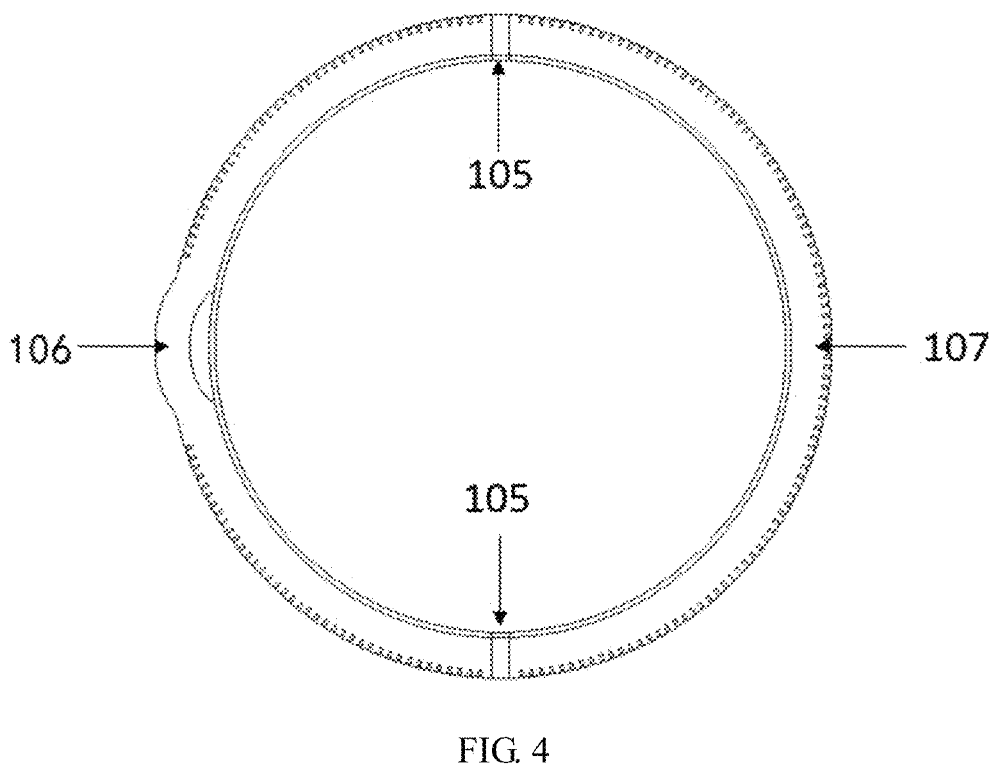
FIG. 4 is a schematic front view of a rotating frame according to some embodiments of the present application.
Figure 5:
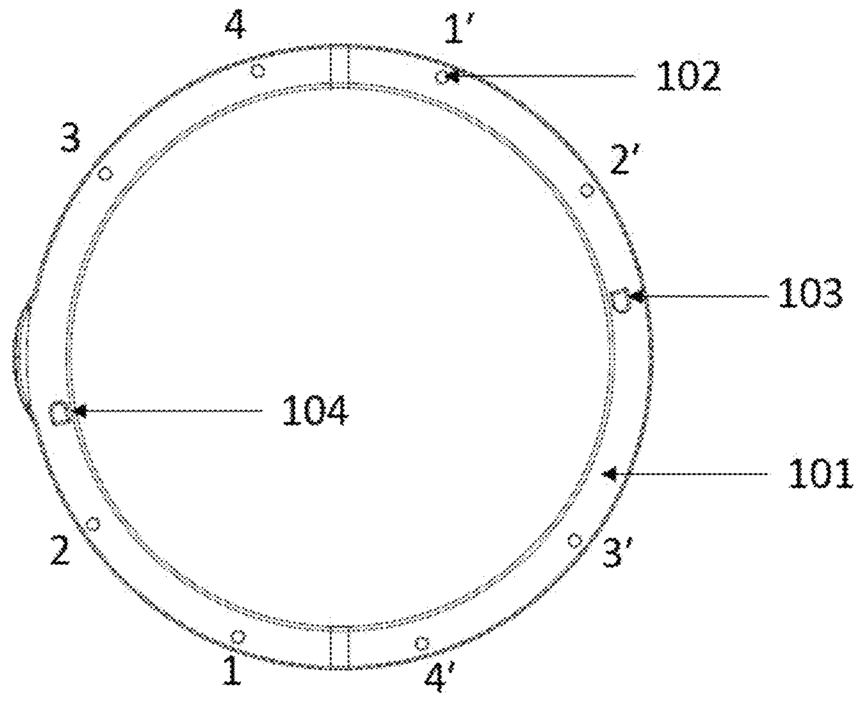
FIG. 5 is a schematic rear view of the rotating frame according to some embodiments of the present application.

As shown in FIG. 3, the rotation angle of the rotating frame 101 relative to the shell 501 is β. The conductive members of the shell 501 include a third ECG conductive member 601 electrically connected to the circuit board 600, a connecting member 602, a first body fat conductive member 603, and a second body fat conductive member 604. As shown in FIG. 5, the rotating frame conductive member 101 includes a first rotating frame conductive member 103 and a second rotating frame conductive member 104 that are provided on the side of the rotating frame 101 facing the shell 501. The third ECG conductive member 601 and the connecting member 602 in FIG. 3 may both be conductive members, such as spring pins.

Figure 2:
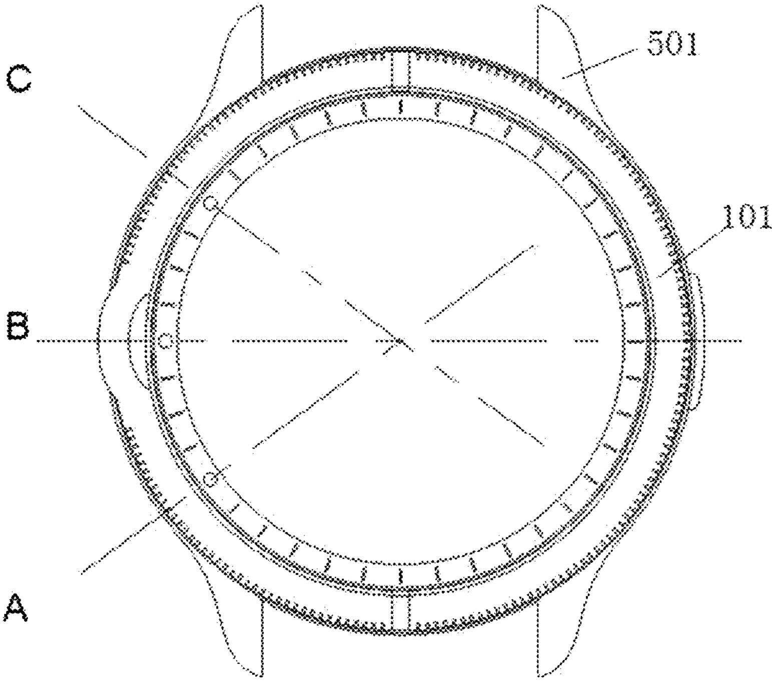
FIG. 2 is a schematic structural view of the electronic device according to some embodiments of the present application.

During use, when the rotating frame 101 rotates to the position shown as A in FIG. 2, the first rotating frame conductive member 103 and the second rotating frame conductive member 104 are respectively connected to the first body fat conductive member 603 and the second body fat conductive member 604. In this way, the first physiological monitoring electrode 106 and the second physiological monitoring electrode 107 are electrically connected to the body fat monitoring circuit 9 respectively. At this time, the users press their two fingers respectively on the first physiological monitoring electrode 106 and the second physiological monitoring electrode 107 of the rotating frame 101 to measure the use's body fat. When the rotating frame 101 rotates to position C as shown in FIG. 2, the first rotating frame conductive member 103 is electrically connected to the third ECG conductive member 601 to achieve electrical conduction between the first physiological monitoring electrode 106 and the ECG monitoring circuit 8. The users may press the first physiological monitoring electrode 106 of the rotating frame 101 with their finger, such that the electrocardiogram monitoring can be realized.

During use, when the third ECG conductive member 601 and the connecting member 602 are both conductive members, and the rotating frame 101 rotates to the position shown as A in FIG. 2, the first rotating frame conductive member 103 and the second rotating frame conduct electricity member 104 are electrically connected to the first body fat conductive member 603 and the second body fat conductive member 604 respectively so that the first physiological monitoring electrode 106 and the second physiological monitoring electrode 107 are electrically connected to the body fat monitoring circuit 9 respectively. At this time, the users may press the first physiological monitoring electrode 106 and the second physiological monitoring electrode 107 of the rotating frame 101 with two fingers respectively, such that the user's body fat can be measured. When the rotating frame 101 rotates to position C as shown in FIG. 2, the first rotating frame conductive member 103 and the second rotating frame conductive member 104 are electrically connected to the third ECG conductive member 601 and the connecting member 602 respectively to, make the first physiological monitoring electrode 106 and the second physiological monitoring electrode 107 electrically connected to the ECG monitoring circuit 8 respectively. The users may press the first physiological monitoring electrode 106 and the second physiological monitoring electrode 107 of the rotating frame 101 respectively with two fingers to realize electrocardiogram monitoring.

In some embodiments, depending on the actual usage, other physiological monitoring circuits can be set up, which are determined based on the actual situation.

Figure 7:
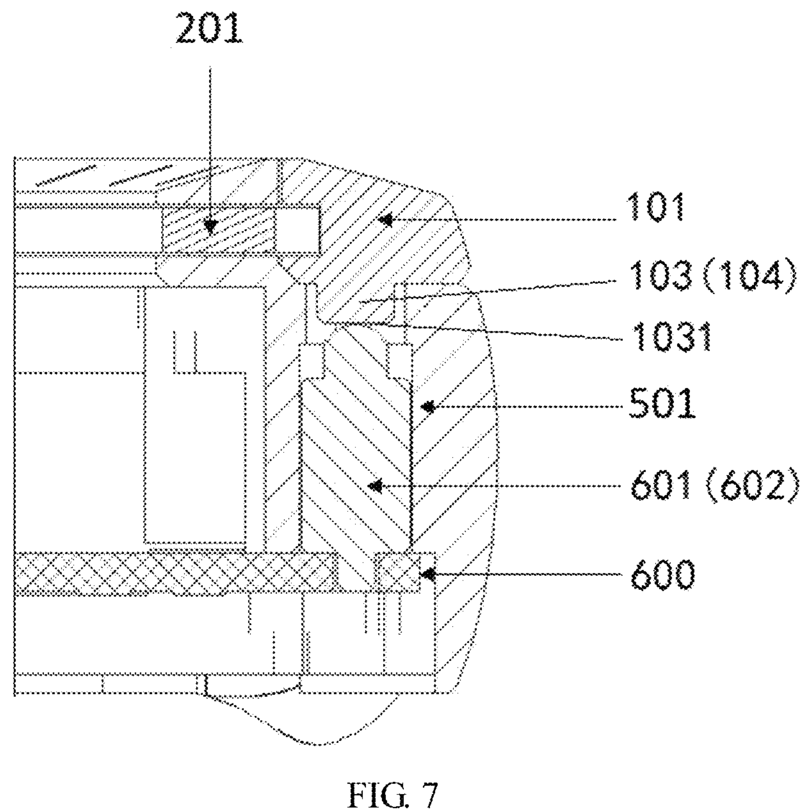
FIG. 7 is a schematic structural view from another viewpoint of the first rotating frame conductive member and the second rotating frame conductive member according to some embodiments of the present application.

In some embodiments, as shown in FIG. 7, the physiological monitoring circuit includes an ECG monitoring circuit 8 and a body fat monitoring circuit 9;

- the first shell conductive member and the second shell conductive member are connected to the ECG monitoring circuit 8 or the body fat monitoring circuit 9 through a switch 7;
- in response to that the rotating frame 101 rotates relative to the shell 501 to a position where the first rotating frame conductive member 103 is in contact with the first shell conductive member, and the second rotating frame conductive member 104 is in contact with the second shell conductive member:
- if the switch 7 is switched to a position where the first shell conductive member is connected to the ECG monitoring circuit 8, the first physiological monitoring electrode 106 is electrically connected to the ECG monitoring circuit 8. The users may press the first physiological monitoring electrode 106 of the rotating frame 101 to realize electrocardiogram monitoring.
- if the switch 7 is switched to a position where both the first shell conductive member and the second shell conductive member are connected to the body fat monitoring circuit 9, the first physiological monitoring electrode 106 and the second physiological monitoring electrode 107 are electrically connected to the body fat monitoring circuit 9 respectively. The users may press the first physiological monitoring electrode 106 and the second physiological monitoring electrode 107 of the rotating frame 101 respectively with two fingers to measure the users' body fat.

In some embodiments, without rotating the rotating frame 101, by clicking on the screen or other operations, the switch 7 can be controlled to switch the connection state, thereby realizing electrocardiogram monitoring or body fat measurement.

In some embodiments, as shown in FIG. 7, the physiological monitoring circuit includes an ECG monitoring circuit 8 and a body fat monitoring circuit 9;

- the first shell conductive member and the second shell conductive member are connected to the ECG monitoring circuit 8 or the body fat monitoring circuit 9 through a switch 7;
- in response to that the rotating frame 101 rotates relative to the shell 501 to a position where the first rotating frame conductive member is in contact with the first shell conductive member, and the second rotating frame conductive member is in contact with the second shell conductive member:
- if the switch 7 is switched to a position where the first shell conductive member and the second shell conductive member are connected to the ECG monitoring circuit 8, the first physiological monitoring electrode 106 and the second physiological monitoring electrode 107 are electrically connected to the ECG monitoring circuit 8 respectively. The users may press the first physiological monitoring electrode 106 and the second physiological monitoring electrode 107 of the rotating frame 101 respectively with two fingers to realize electrocardiogram monitoring.
- if the switch 7 is switched to a position where the first shell conductive member and the second shell conductive member are connected to the body fat monitoring circuit 9, the first physiological monitoring electrode 106 and the second physiological monitoring electrode 107 are electrically connected to the body fat monitoring circuit 9 respectively. The users may press the first physiological monitoring electrode 106 and the second physiological monitoring electrode 107 of the rotating frame 101 respectively with two fingers to measure the user's body fat.

In some embodiments, the rotating frame 101 is made of metal, and this metal material can be used as an electrode. The first physiological monitoring electrode 106 and the second physiological monitoring electrode 107 are respectively parts of the metal material in the rotating frame 101.

In some embodiments, a part of the rotating frame 101 is directly used as a physiological monitoring electrode, which avoids the need to install additional electrodes on the rotating frame 101, thereby simplifying the structure of the rotating frame 101, facilitating processing of the rotating frame 101, and reducing costs.

In some embodiments, an insulator 105 is provided between the first physiological monitoring electrode 106 and the second physiological monitoring electrode 107 to prevent the first physiological monitoring electrode 106 from contacting and conducting the second physiological monitoring electrode 107.

As shown in FIG. 1, the first physiological monitoring electrode 106 and the second physiological monitoring electrode 107 are provided symmetrically about a certain radial direction of the rotating frame 101, and the first physiological monitoring electrode 106 and the second physiological monitoring electrode 107 are provided with an insulator 105 with a narrow width to ensure that the sizes of the first physiological monitoring electrode 106 and the second physiological monitoring electrode 107 meet the requirements as much as possible. The insulator 105 can be made of insulating rubber or other materials.

In these embodiments, the first physiological monitoring electrode 106 and the second physiological monitoring electrode 107 are directly provided on the rotating frame 101 and are separated by the insulator 105, so that the circumferential space of the rotating frame 101 can be fully utilized, the functions of the rotating frame 101 can be ensured, and the structure of the rotating frame 101 can be simplified as much as possible.

In some embodiments, it is necessary to ensure the insulation between the shell 501 and the first physiological monitoring electrode 106 or the second physiological monitoring electrode 107, the shell 501 is made of insulating material; or

- at least one of a surface of the rotating frame 101 contacting the shell 501 and a surface of the shell 501 contacting the rotating frame 101 is provided with an insulating coating. In this way, the shell 501 is insulated from the first physiological monitoring electrode 106 and the second physiological monitoring electrode 107.

In some embodiments, both the first rotating frame conductive member 103 and the second rotating frame conductive member 104 are protrusions provided on the rotating frame 101, and both the first shell conductive member and the second shell conductive member are spring pins.

The arrangement of the protrusions and spring pins makes the contact between the conductive members of the shell 501 and the conductive members of the rotating frame 101 more reliable, and provides a certain tactile feedback during the rotation.

The shell 501 is provided with a guide groove 505 for accommodating the spring pin, and the opening of the guide groove 505 faces the side of the rotating frame 101 with the protrusion. The guide groove 505 is provided to guide and limit the spring pin, so as to ensure that the conductive members of the shell 501 and the conductive members of the rotating frame 101 can contact smoothly and achieve electrical connection.

Figure 6:
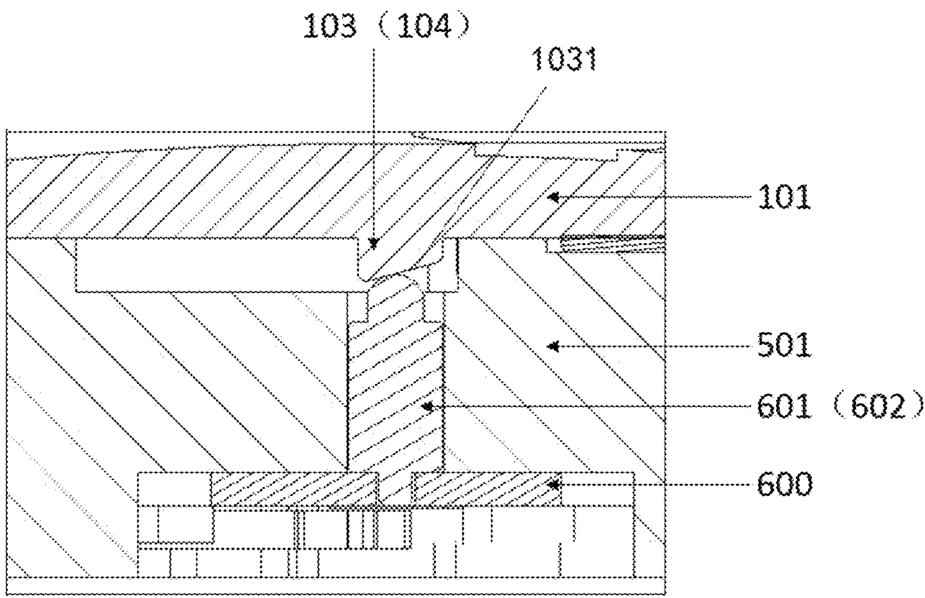
FIG. 6 is a schematic structural view of a first rotating frame conductive member and a second rotating frame conductive member according to a first embodiment of the present application.

As shown in FIG. 6 and FIG. 7, the protrusions are provided with an inclined surface 1031 in contact with the spring pins. The inclined direction of the inclined surface 1031 is shown in FIG. 6. During the rotation of the rotating frame 101, the arrangement of the inclined surface 1031 can increase the contact area between the protrusion and the spring pin, and improve the reliability of the electrical connection between the protrusion and the spring pin.

In some embodiments, the electronic device further includes a gear limiting mechanism. The gear limiting mechanism includes at least one elastic member 301 and at least one groove 102 for cooperating with the at least one elastic member 301, one of the elastic member 301 and the groove 102 is provided on the shell 501, and the other is provided on the rotating frame 101, and in response to that the rotating frame 101 rotates to a preset position relative to the shell 501, the elastic member 301 is engaged with the corresponding groove 102.

Figures 9, 10:
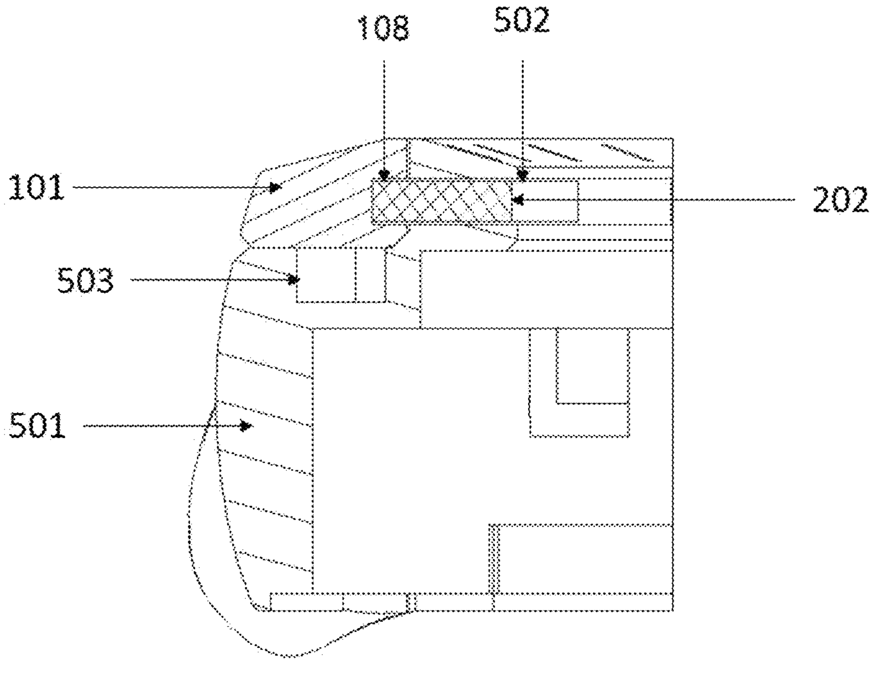
FIG. 9 is a schematic cross-sectional view of the electronic device along a direction perpendicular to the direction shown in FIG. 8 according to some embodiments of the present application.
FIG. 10 is a schematic view of a groove cooperating with an elastic component in the electronic device according to some embodiments of the present application.

As shown in FIG. 10, the elastic member 301 includes a spring 302 and a ball 303. The shell 501 is provided with a mounting hole for installing the elastic member 301. During the rotation of the rotating frame 101, when the groove 102 is rotated to the point where the groove 102 matches the elastic member 301, under the elastic force of the spring 302, the ball 303 moves upward and partially enters the groove 102, so that the ball 303 and the groove 102 are engaged with each other to limit the position, and at the same time a certain tactile feedback about engagement is provides. If the rotating frame 101 keeps rotating, the groove 102 leaves the elastic member 301, and the ball 303 comes out of the groove 102.

The arrangement of the elastic member 301 and the groove 102 in these embodiments allows the user to have a good tactile feedback experience when rotating the rotating frame 101 to different positions, thereby facilitating switching different gears. As shown in FIG. 2, the three positions A, B, and C represent three different gears. When the marked part of the rotating frame 101 rotates to the three positions A, B, and C, it represents different gears.

In some embodiments, as shown in FIG. 2, the rotating frame 101 rotates relative to the shell 501 within the angle range from A to C. When the marking part of the rotating frame 101 rotates to the A position, the body fat monitoring function of the electronic device is turned on. If the users press the first physiological monitoring electrode 106 and the second physiological monitoring electrode 107 of the rotating frame 101 with their two fingers, the users' body fat can be measured. When the marking part of the rotating frame 101 rotates to the B position, the payment function of the electronic device is turned on, and the user can operate the payment function. When the marking part of the rotating frame 101 rotates to the C position, the ECG function is turned on. The users may press the fingers on the first physiological monitoring electrode 106 and the second physiological monitoring electrode 107 of the frame 101, such that electrocardiogram monitoring can be realized.

Depending on the actual situation, the functions corresponding to the three gears A, B, and C can be adjusted, or the sports mode can be turned on, and the user can perform other functions such as outdoor, indoor, and swimming.

Figure 11:
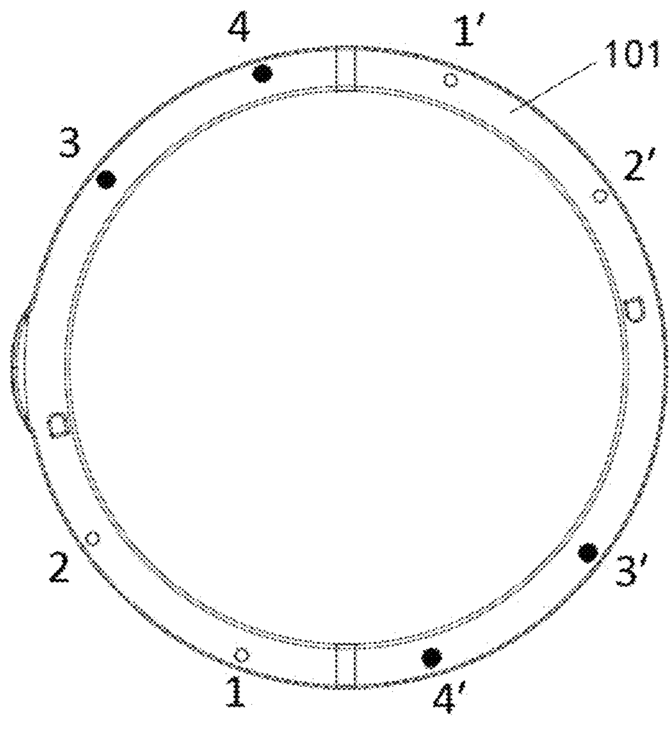
FIG. 11 is a schematic structural view of the groove of the rotating frame according to a first embodiment of the present application.
Figure 12:
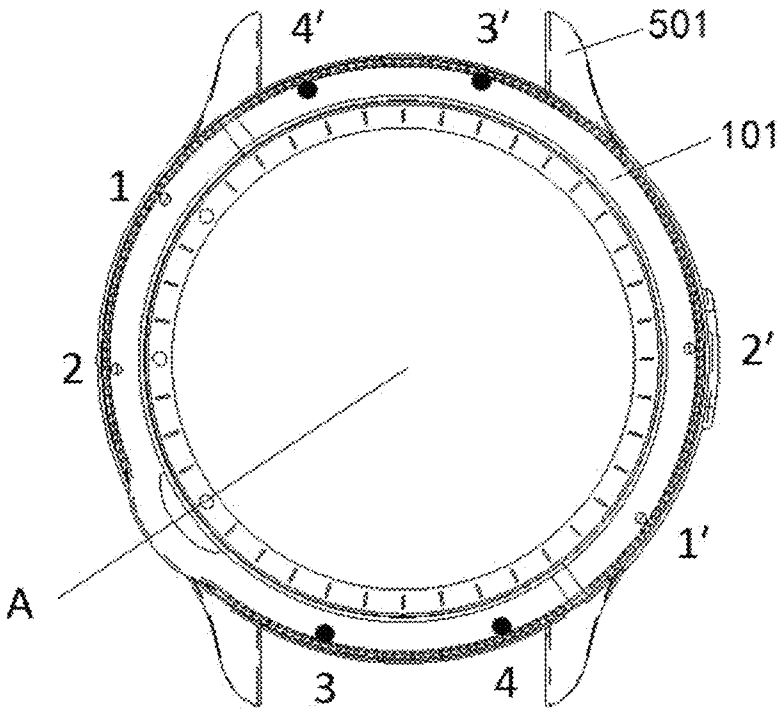
FIG. 12 is a schematic view of the elastic component cooperating with groove the when the rotating frame rotates to a gear A according to some embodiments of the present application.

As shown in FIG. 11, the positions indicated by 1, 2, 3, 4, 1', 2', 3' and 4' are different positions in the circumferential direction of the rotating frame 101, and grooves 102 are provided on the positions 1, 2, 3, 4, 1', 2', 3' and 4' in the circumferential direction of the rotating frame 101. As shown in FIG. 12, the positions indicated by 1, 2, 3, 4, 1', 2', 3' and 4' are different positions in the circumferential direction of the shell 501, and elastic members 301 are provided at positions 3, 4, 3', and 4' in the circumferential direction of the shell 501. When the rotating frame 101 rotates to the angular position shown in A in FIG. 12, the grooves 102 located at positions 3, 4, 3' and 4' in the circumferential direction of the rotating frame 101 respectively cooperate with the elastic members 301 provided at positions 3, 4, 3', and 4' in the circumferential direction of the shell 501, thereby achieving the position limit of A gear and tactile feedback.

Figure 13:
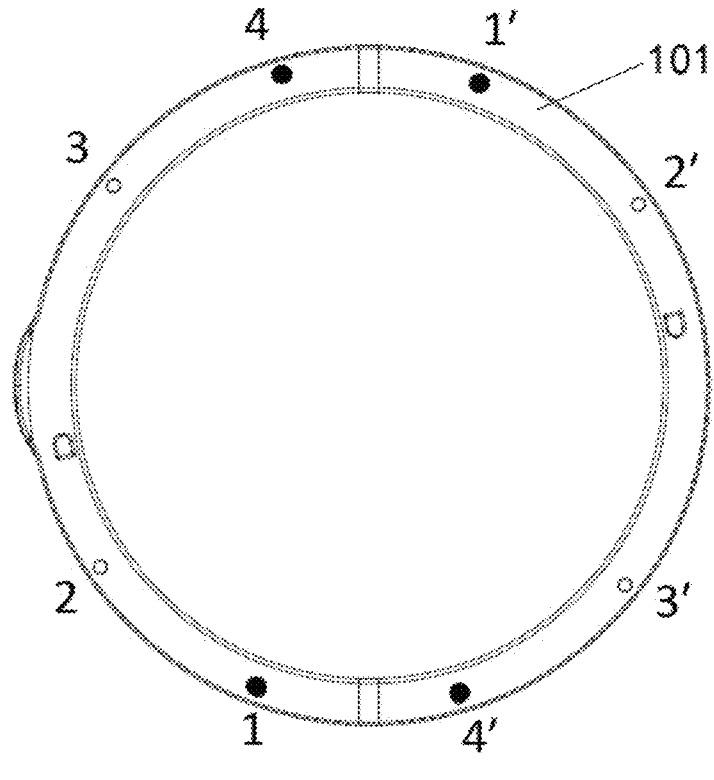
FIG. 13 is a schematic structural view of the groove of the rotating frame according to a second embodiment of the present application.
Figure 14:
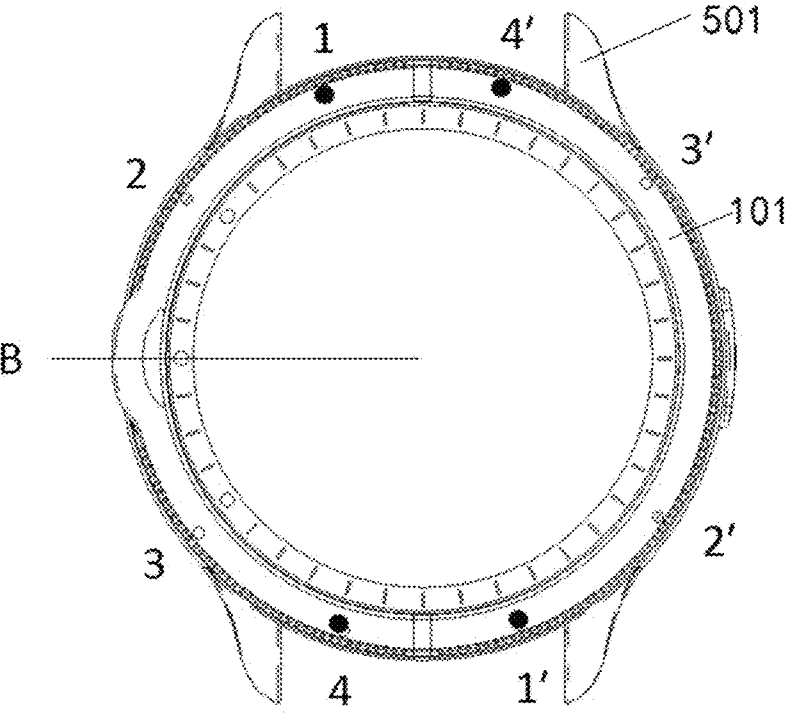
FIG. 14 is a schematic view of the elastic component cooperating with groove the when the rotating frame rotates to a gear B according to some embodiments of the present application.

As shown in FIG. 13, the positions indicated by 1, 2, 3, 4, 1', 2', 3' and 4' are different positions in the circumferential direction of the rotating frame 101, and grooves 102 are provided on the positions 1, 2, 3, 4, 1', 2', 3' and 4' in the circumferential direction of the rotating frame 101. As shown in FIG. 14, the positions indicated by 1, 2, 3, 4, 1', 2', 3' and 4' are different positions in the circumferential direction of the shell 501, and elastic members 301 are provided at positions 1, 4, 1', and 4' in the circumferential direction of the shell 501. When the rotating frame 101 rotates to the angular position shown in B in FIG. 14, the grooves 102 located at positions 1, 4, l' and 4' in the circumferential direction of the rotating frame 101 respectively cooperate with the elastic members 301 provided at positions 1, 4, l' and 4' in the circumferential direction of the shell 501, thereby achieving the position limit of B gear and tactile feedback.

Figure 15:
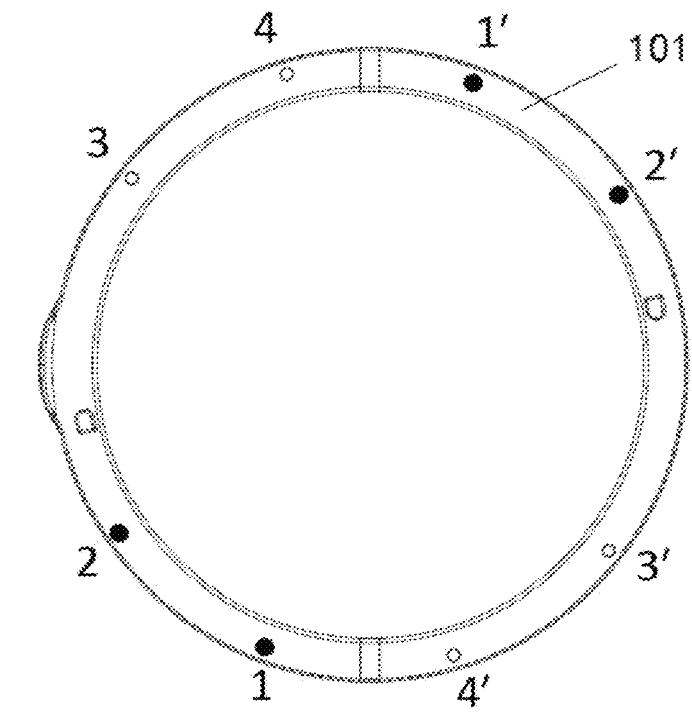
FIG. 15 is a schematic structural view of the groove of the rotating frame according to a third embodiment of the present application.
Figure 16:
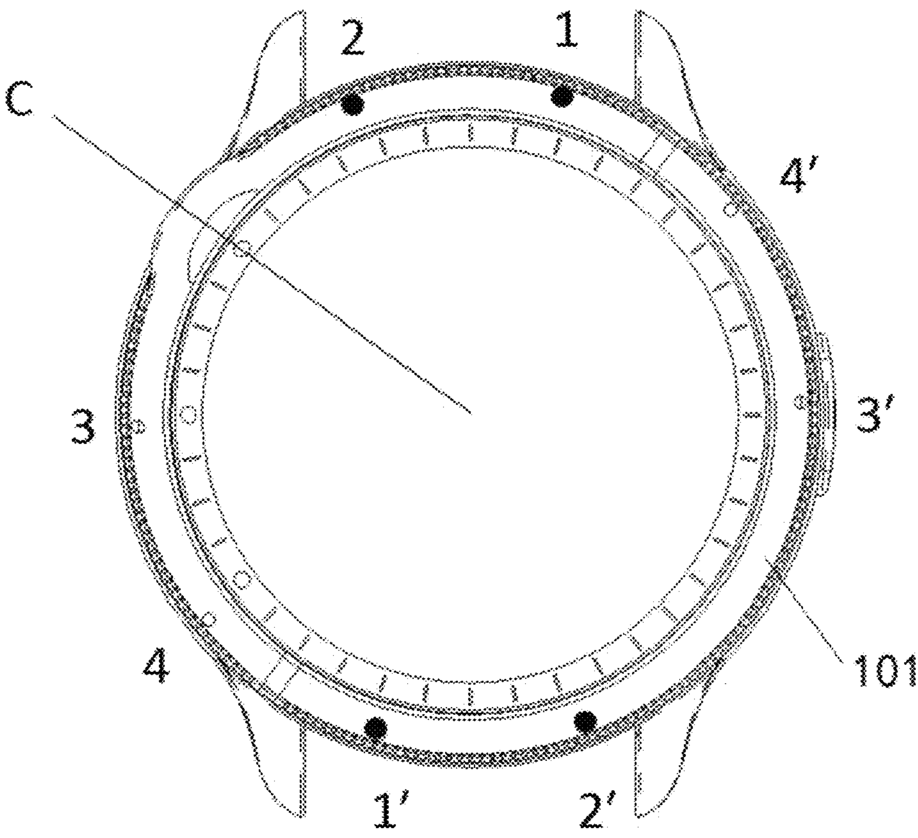
FIG. 16 is a schematic view of the elastic component cooperating with groove the when the rotating frame rotates to a gear C according to some embodiments of the present application.
Figure 17:
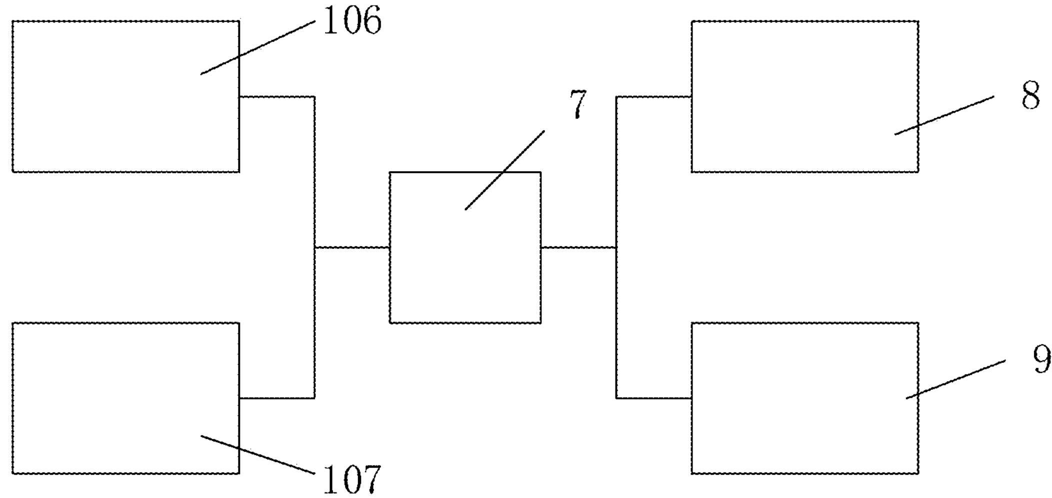
FIG. 17 is a schematic view of a connection relationship of a first physiological monitoring electrode, a second physiological monitoring electrode, and a physiological monitoring circuit according to some embodiments of the present application.

As shown in FIG. 15, the positions indicated by 1, 2, 3, 4, 1', 2', 3' and 4' are different positions in the circumferential direction of the rotating frame 101, and grooves 102 are provided on the positions 1, 2, 3, 4, 1', 2', 3' and 4' in the circumferential direction of the rotating frame 101. As shown in FIG. 16, the positions indicated by 1, 2, 3, 4, 1', 2', 3' and 4' are different positions in the circumferential direction of the shell 501, and elastic members 301 are provided at positions 1, 2, 1', and 2' in the circumferential direction of the shell 501. When the rotating frame 101 rotates to the angular position shown in C in FIG. 16, the grooves 102 located at positions 1, 2, l' and 2' in the circumferential direction of the rotating frame 101 respectively cooperate with the elastic members 301 provided at positions 1, 2, l' and 2' in the circumferential direction of the shell 501, thereby achieving the position limit of C gear and tactile feedback.

Depending on the actual situation, you can set one gear, two gears, four, five, etc., which will be determined based on the actual situation.

In some embodiments, the shell 501 is provided with a guide chute 503 with an annular part, a side of the rotating frame 101 facing the shell 501 is provided with a guide protrusion that cooperates with the guide chute 503, and the guide protrusion is configured to insert into the guide chute 503 and slide along the guide chute 503.

As shown in FIG. 3, the shell 501 is provided with two arc-shaped guide chute 503, and the central angle corresponding to the guide chute 503 is β. The central angle β is related to the rotation of the rotating frame 101 relative to the shell 501. As shown in FIG. 5, there are two first rotating frame conductive members 103 and second rotating frame conductive members 104 corresponding to the two guide chute 503 in FIG. 14. The first rotating frame conductive member 103 and the second rotating frame conductive member 104 are protrudingly provided. While realizing conduction, the first rotating frame conductive member 103 and the second rotating frame conductive member 104 respectively cooperate with the guide chute 503 in FIG. 3.

Figure 8:
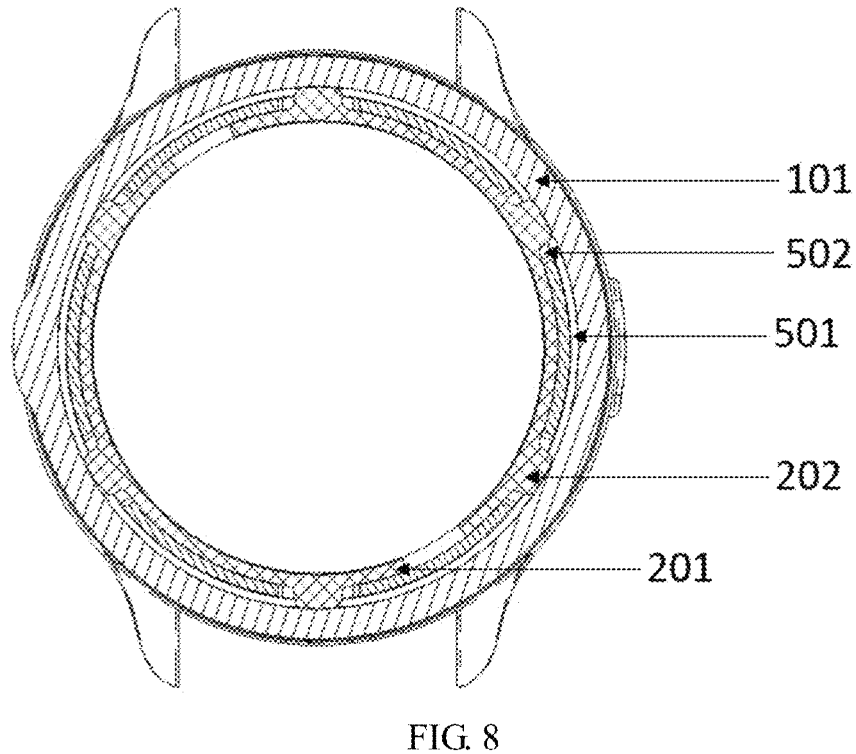
FIG. 8 is a schematic view of the shell cooperating with a collar in the electronic device according to some embodiments of the present application.

As shown in FIG. 1, FIG. 8 and FIG. 9, the electronic device includes a shell 501, a rotating frame 101 and a clamping member. The shell 501 is provided with a receiving groove for accommodating at least part of the rotating frame 101, and the rotating frame 101 is rotatably provided on the shell 501. The side wall of the receiving groove is provided with a through hole 502. The rotating frame 101 is provided with a snap groove 108. The clamping member is provided in the shell 501 and is protrudingly provided with at least one snap tab 202. The snap tab 202 is configured to pass through the through hole 502 and engage with the snap groove 108 to prevent the rotating frame 101 from being separated from the shell 501.

It should be noted that the rotation angle of the rotating frame 101 relative to the shell 501 may be 360° in the circumferential direction, or may be other angles less than 360°, which is determined based on the actual situation.

The receiving groove may be provided on the surface of the shell 501 along the outer periphery of the shell 501, or may be provided on part of the surface of the shell 501, which is determined based on the actual situation.

The through hole 502 can be provided on the inner wall of the receiving groove. In this case, the snap groove 108 is provided on the side of the rotating frame 101 facing the inner wall of the receiving groove, and the through hole 502 can also be provided on the outer wall of the receiving groove. In this case, the through hole 502 can be provided on the inner wall of the receiving groove. In this case, the snap groove 108 is provided on the side of the rotating frame 101 facing the outer wall of the receiving groove.

In some embodiments, the rotating frame 101 is provided with anti-slip protrusions to facilitate the rotating operation of the rotating frame 101.

The rotation frame 101 may be a circular frame or other shapes, which may be determined based on the actual situation.

During the use of the electronic device provided by these embodiments, when maintenance is required, the clamping member can be taken out from the shell 501 and the snap tab 202 can be released from the snap groove 108. At this time, the rotating frame 101 can be removed from the shell 501. After the repair is completed, the rotating frame 101 can be placed in the receiving groove of the shell 501, then the clamping member can also be placed in the shell 501, and the snap tab 202 of the clamping member can pass through the through hole 502 and engage with the snap groove 108. As shown in FIG. 9, the installation of the rotating frame 101 can be completed. During use, the rotating frame 101 can be rotated as needed.

Compared with the related art, the disassembly and assembly process of the rotating frame 101 of the electronic device provided by these embodiments is convenient, and the rotating frame 101 will not be damaged during the disassembly and assembly process. Frequent replacement of the rotating frame 101 can be avoided, which is beneficial to extend the service life of the rotating frame 101 and reduce maintenance costs.

In some embodiments, one snap groove 108 is provided, and the snap groove 108 is an annular groove 102 provided on the rotating frame 101. The annular groove 102 is in the shape of a closed ring in the circumferential direction. During the rotation of the rotating frame 101, the rotation angle of the rotating frame 101 is not limited, so that the rotating frame 101 can achieve 360° rotation in the circumferential direction.

If the rotation angle of the rotating frame 101 needs to be set to less than 360°, an additional angle limiting structure can be provided to limit the rotation angle of the rotating frame 101 relative to the shell 501.

In some embodiments, the clamping member is an elastic collar 201, and the snap tab 202 protrudes along the radial direction of the elastic collar 201 and is disposed on the outside of the elastic collar 201.

In some embodiments, the snap tab 202 and the elastic collar 201 have an integrated structure, and the thickness of the tab 202 is the same as the thickness of the elastic collar 201.

The shell 501 is provided with a position for installing the elastic collar 201. After installation, the elastic collar 201 will in tightly contact with the shell 501 because of the elasticity, and the snap tab 202 passes through the through hole 502 and engages with the snap groove 108.

In some embodiments, a groove hole 504 is provided on the contact surface of the shell 501 and the rotating frame 101, and a lubricating sheet 401 is attached inside to reduce the friction between the rotating frame 101 and the shell 501.

As shown in FIG. 1, four lubricating sheets 401 are provided, and the lubricating sheets 401 have an arc-shaped structure. In some embodiments, the lubricating sheets can be evenly provided along the circumferential direction of the shell 501.

In some embodiments, the electronic device is a smart watch, and the smart watch further includes a dial provided on the shell 501. The rotating frame 101 is configured to surround the dial. Moreover, the rotating frame 101 is a ring-shaped bezel, and the bezel can be rotated during use. In some embodiments, the electronic device can also be other types of products, which are determined according to actual conditions.

Among the first rotating frame conductive member 103, the second rotating frame conductive member 104, the first physiological monitoring electrode 106, the second physiological monitoring electrode 107, the first ECG conductive member, the second ECG conductive member, the third ECG conductive members 601, the first body fat conductive member 603 and the second body fat conductive member 604 mentioned in the present application, the "first" and "second" are only to distinguish the difference in position, not to indicate the order.

Each embodiment in this specification is described in a progressive manner. Each embodiment focuses on its differences from other embodiments. The same and similar parts between the various embodiments can be referred to each other. Any combination of all the embodiments provided by the present application is within the protection scope of the present application and will not be described again.

The electronic device provided by the present application has been introduced in detail above. This article uses specific examples to illustrate the principles and implementation methods of the present application. The description of the above embodiments is only used to help understand the method and the core idea of the present application. It should be noted that those skilled in the art can make several improvements and modifications to the present application without departing from the principles of the present application, and these improvements and modifications also fall within the scope of the claims of the present application.

What is claimed is:

1. An electronic device, comprising:

a shell and a rotating frame rotatably provided outside a part of the shell;

wherein the rotating frame is provided with a first physiological monitoring electrode, a second physiological monitoring electrode, a first rotating frame conductive member electrically connected to the first physiological monitoring electrode, and a second rotating frame conductive member electrically connected to the second physiological monitoring electrode;

a physiological monitoring circuit is provided in the shell, and the shell is provided with a first shell conductive member electrically connected to the physiological monitoring circuit and a second shell conductive member electrically connected to the physiological monitoring circuit;

in response to that the rotating frame rotates to a preset position relative to the shell, the first rotating frame conductive member is in contact with the first shell conductive member, and the second rotating frame conductive member is in contact with the second shell conductive member, so that the first physiological monitoring electrode and the second physiological monitoring electrode are electrically connected to the physiological monitoring circuit respectively; and both the first rotating frame conductive member and the second rotating frame conductive member are protrusions provided on the rotating frame, and both the first shell conductive member and the second shell conductive member are spring pins.

2. The electronic device of claim 1, wherein the physiological monitoring circuit is an electrocardiogram (ECG) monitoring circuit; and in response to that the rotating frame rotates to a first position relative to the shell, the first rotating frame conductive member is in contact with the first shell conductive member, and the second rotating frame conductive member is in contact with the second shell conductive member, so that the first physiological monitoring electrode and the second physiological monitoring electrode are electrically connected to the ECG monitoring circuit respectively.

3. The electronic device of claim 1, wherein the physiological monitoring circuit is an ECG monitoring circuit; and in response to that the rotating frame rotates to a first position relative to the shell, the first rotating frame conductive member is in contact with the first shell conductive member, and the second rotating frame conductive member is in contact with the second shell conductive member, so that the first physiological monitoring electrode or the second physiological monitoring electrode are electrically connected to the ECG monitoring circuit.

4. The electronic device of claim 1, wherein the physiological monitoring circuit is a body fat monitoring circuit; and in response to that the rotating frame rotates to a second position relative to the shell, the first rotating frame conductive member is in contact with the first shell conductive member, and the second rotating frame conductive member is in contact with the second shell conductive member, so that the first physiological monitoring electrode and the second physiological monitoring electrode are electrically connected to the body fat monitoring circuit respectively.

5. The electronic device of claim 1, wherein the physiological monitoring circuit comprises an ECG monitoring circuit and a body fat monitoring circuit; the first shell conductive member comprises a first ECG conductive member electrically connected to the ECG monitoring circuit and a first body fat conductive member electrically connected to the body fat monitoring circuit, and the second shell conductive member comprises a second ECG conductive member electrically connected to the ECG monitoring circuit and a second body fat conductive member electrically connected to the body fat monitoring circuit;

in response to that the rotating frame rotates to a first position relative to the shell, the first rotating frame conductive member is in contact with the first ECG conductive member, and the second rotating frame conductive member is in contact with the second ECG conductive member, so that the first physiological monitoring electrode and the second physiological monitoring electrode are electrically connected to the ECG monitoring circuit respectively; and in response to that the rotating frame rotates to a second position relative to the shell, the first rotating frame conductive member is in contact with the first body fat conductive member, and the second rotating frame conductive member is in contact with the second body fat conductive member, so that the first physiological monitoring electrode and the second physiological monitoring electrode are electrically connected to the body fat monitoring circuit respectively.

6. The electronic device of claim 1, wherein the physiological monitoring circuit comprises an ECG monitoring circuit and a body fat monitoring circuit; the first shell conductive member comprises a third ECG conductive member electrically connected to the ECG monitoring circuit and a first body fat conductive member electrically connected to the body fat monitoring circuit, and the second shell conductive member comprises a second body fat conductive member electrically connected to the body fat monitoring circuit;

in response to that the rotating frame rotates to a first position relative to the shell, the first rotating frame conductive member is in contact with the third ECG conductive member, so that the first physiological monitoring electrode is electrically connected to the ECG monitoring circuit; and in response to that the rotating frame rotates to a second position relative to the shell, the first rotating frame conductive member is in contact with the first body fat conductive member, and the second rotating frame conductive member is in contact with the second body fat conductive member, so that the first physiological monitoring electrode and the second physiological monitoring electrode are electrically connected to the body fat monitoring circuit respectively.

7. The electronic device of claim 6, wherein the second shell conductive member comprises a connecting member; and in response to that the rotating frame rotates to the first position relative to the shell, the first rotating frame conductive member is in contact with the third ECG conductive member, and the connecting member is in contact with the second rotating frame conductive member.

8. The electronic device of claim 1, wherein the physiological monitoring circuit comprises an ECG monitoring circuit and a body fat monitoring circuit;

the first shell conductive member and the second shell conductive member are connected to the ECG monitoring circuit or the body fat monitoring circuit through a switch; when the rotating frame rotates relative to the shell to a position where the first rotating frame conductive member is in contact with the first shell conductive member, and the second rotating frame conductive member is in contact with the second shell conductive member:

in response to that the switch is switched to a position where the first shell conductive member and the second shell conductive member are connected to the ECG monitoring circuit, the first physiological monitoring electrode and the second physiological monitoring electrode are electrically connected to the ECG monitoring circuit respectively; and in response to that the switch is switched to a position where the first shell conductive member and the second shell conductive member are connected to the body fat monitoring circuit, the first physiological monitoring electrode and the second physiological monitoring electrode are electrically connected to the body fat monitoring circuit respectively.

9. The electronic device of claim 1, wherein the physiological monitoring circuit comprises an ECG monitoring circuit and a body fat monitoring circuit;

the first shell conductive member and the second shell conductive member are connected to the ECG monitoring circuit or the body fat monitoring circuit through a switch; when the rotating frame rotates relative to the shell to a position where the first rotating frame conductive member is in contact with the first shell conductive member, and the second rotating frame conductive member is in contact with the second shell conductive member:

in response to that the switch is switched to a position where the first shell conductive member is connected to the ECG monitoring circuit, the first physiological monitoring electrode is electrically connected to the ECG monitoring circuit; and in response to that the switch is switched to a position where both the first shell conductive member and the second shell conductive member are connected to the body fat monitoring circuit, the first physiological monitoring electrode and the second physiological monitoring electrode are electrically connected to the body fat monitoring circuit respectively.

10. The electronic device of claim 1, wherein an insulator is provided between the first physiological monitoring electrode and the second physiological monitoring electrode to prevent the first physiological monitoring electrode from contacting and conducting the second physiological monitoring electrode.

11. The electronic device of claim 1, wherein part of the rotating frame is made of metal, and the first physiological monitoring electrode and the second physiological monitoring electrode are respectively the part of the rotating frame made of metal.

12. The electronic device of claim 11, wherein the shell is made of insulating material; or at least one of a surface of the rotating frame contacting the shell and a surface of the shell contacting the rotating frame is provided with an insulating coating.

13. The electronic device of claim 1, wherein the protrusions are provided with an inclined surface in contact with the spring pins.

14. The electronic device of claim 1, further comprising:

a gear limiting mechanism comprising at least one elastic component and at least one groove for cooperating with the at least one elastic component;

wherein one of the elastic component and the groove is provided on the shell, and the other of the elastic component and the groove is provided on the rotating frame, and in response to that the rotating frame rotates to a preset position relative to the shell, the elastic component is engaged with the corresponding groove.

15. The electronic device of claim 1, wherein the shell is provided with a guide chute with an annular part; a side of the rotating frame facing the shell is provided with a guide protrusion cooperated with the guide chute, and the guide protrusion is configured to insert into the guide chute and slide along the guide chute.

16. The electronic device of claim 1, wherein the electronic device is a smart watch; the smart watch further comprises a dial provided on the shell, and the rotating frame is configured to surround the dial.

* * * * *